United States Patent [19]　[11] 3,950,539
Militzer et al.　[45] Apr. 13, 1976

[54] SUBSTITUTED DIAMINOGUANIDINES

[75] Inventors: Hans Militzer, Hofheim, Taunus;
Erhardt Winkelmann, Kelkheim, Taunus; Wolfgang Raether, Dreieichenhain, all of Germany

[73] Assignee: Hoechst Aktiengesellschaft, Frankfurt am Main, Germany

[22] Filed: Feb. 19, 1975

[21] Appl. No.: 550,917

[30] Foreign Application Priority Data

Feb. 21, 1974　Germany............................ 2408289

[52] U.S. Cl.......... 424/324; 260/465 C; 260/558 R; 260/558 P; 260/559 R; 260/564 F; 260/566 B; 424/304
[51] Int. Cl.².............. A61K 31/165; C07C 103/22
[58] Field of Search......... 260/558 H, 558 P, 564 F, 260/559 R; 424/324

[56] References Cited
UNITED STATES PATENTS 3,206,478　9/1965　Marxer et al................... 260/558 H
3,621,056　11/1971　Houlihan et al............. 260/564 F X
3,632,645　1/1972　Bream et al..................... 424/324 X
3,634,508　1/1972　Bream et al..................... 424/324 X
3,769,432　10/1973　Tomcufcik.................. 260/564 F X
3,795,692　3/1974　Kulsa et al................... 260/564 F X
3,816,530　6/1974　Linn................................. 260/564 F
3,856,975　12/1974　Linn................................ 424/324 X
3,901,944　8/1975　Tomcufcik...................... 260/564 F

OTHER PUBLICATIONS

Reid et al., CA 74:63426s, (1971).

Kantor et al., CA 73:24293f, (1970).

Primary Examiner—Robert V. Hines
Assistant Examiner—Thomas A. Waltz
Attorney, Agent, or Firm—Curtis, Morris & Safford

[57] ABSTRACT

Substituted diamino-guanidines are described as well as their manufacture and their use as medicaments against protozoa, especially against coccidiosis.

8 Claims, No Drawings

SUBSTITUTED DIAMINOGUANIDINES 1,3-Bis-(p-chlorobenzylideneamino)-guanidine is known as an agent against coccidiosis (S. Kantor, R. L. Kennett, E. Waletzky, A. S. Tomoufcik, Science 168, 3929 (1970)). However its action, and particularly its compatibility, is not always satisfactory.

The present invention relates to substituted diaminoguanidines of the general formula I

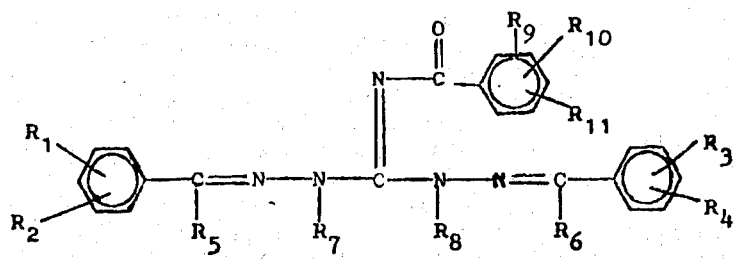

wherein $R_1$ and $R_3$ denote hydrogen, halogen, such as fluorine, chlorine, bromine or iodine, trifluoromethyl or nitrile, $R_2$ and $R_4$ denote hydrogen, halogen, such as fluorine, chlorine, bromine or iodine, $R_5$, $R_6$, $R_7$ and $R_8$ denote hydrogen or alkyl with 1 to 6 C atoms, $R_9$ denotes hydrogen, halogen, such as fluorine, chlorine, bromine or iodine, alkyl, alkoxy with 1 to 6 C atoms in each case, nitrile, trifluoromethyl or nitro, $R_{10}$ denotes hydrogen, halogen, such as fluorine, chlorine, bromine or iodine, or alkyl or alkoxy with 1 to 6 C atoms in each case and $R_{11}$ denotes hydrogen, halogen, such as fluorine, chlorine, bromine or iodine, or alkyl or alkoxy with 1 to 6 C atoms in each case and their pharmacologically acceptable salts.

Those compounds of the general formula I wherein $R_2$, $R_4$, $R_5$, $R_6$, $R_7$ and $R_8$ ... hydrogen, $R_1$ and $R_3$ ... halogen, such as fluorine, chlorine, bromine or iodine, and $R_9$, $R_{10}$ and $R_{11}$ have the meanings indicated above for formula I are preferred. Among these compounds, especially effective are those in which $R_2$, $R_4$, $R_5$, $R_6$, $R_7$, $R_8$, $R_9$ and $R_{10}$ each is hydrogen, $R_1$ and $R_2$ are para-chlorine and $R_{11}$ is hydrogen, Para-chlorine, para-nitro or meta-nitro.

The invention also relates to a process for the manufacture of substituted diaminoguanidines of the general formula I, characterised in that a. an acylisocyanide-dihalide of the formula II

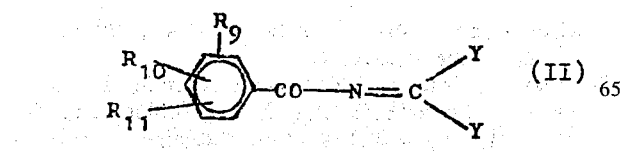

wherein $R_9$, $R_{10}$ and $R_{11}$ have the meanings indicated for formula I and Y denotes halogen, such as fluorine, chlorine or bromine, is reacted with a hydrazone of the formula III

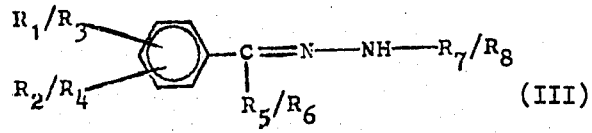

wherein the substituents $R_1$ to $R_8$ have the indicated meanings, with the proviso that $R_1$ should be identical to $R_3$, $R_2$ should be identical to $R_4$, $R_5$ should be identical to $R_6$ and $R_7$ should be identical to $R_8$, or b. an acylisocyanide-dihalide of the formula II is reacted with a hydrazone of the formula IV

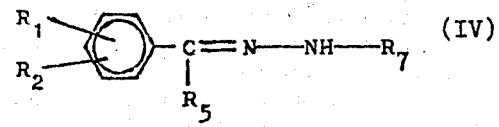

wherein $R_1$, $R_2$, $R_5$ and $R_7$ have the meanings indicated for formula I, and the resulting monohalogen compound of the formula V

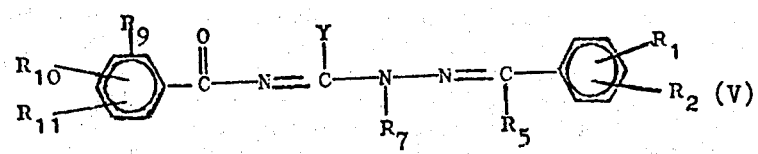

wherein $R_1$, $R_2$, $R_7$, $R_9$, $R_{10}$ and $R_{11}$ have the meanings indicated for formula I and Y denotes halogen, such as fluorine, chlorine or bromine, is reacted with a hydrazone of the formula VI

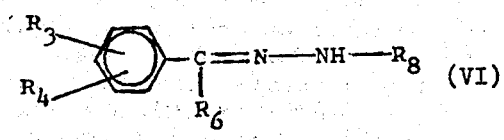

wherein $R_3$, $R_4$ and $R_8$ have the meanings indicated for formula I, or c. a substituted diaminoguanidine of the formula VII

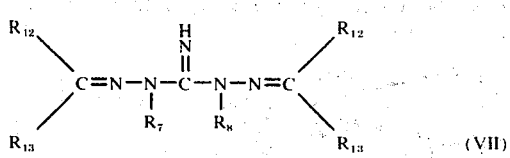

wherein $R_{12}$ and $R_{13}$ denote alkyl with 1 to 6 C atoms, or these two substituents conjointly denote members of an isocyclic ring with 5 to 7 C atoms, and $R_7$ and $R_8$ have the meanings indicated for formula I, is reacted with a halide, such as a chloride or bromide, or an anhydride of an acid of the formula VIII

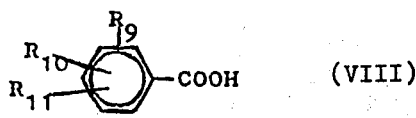

wherein $R_9$, $R_{10}$ and $R_{11}$ have the meanings indicated for formula I, and with a carbonyl compound of the formula IX

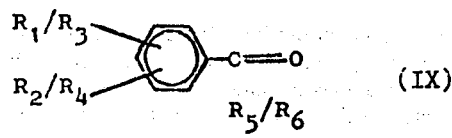

wherein $R_1$, $R_2$, $R_3$, $R_4$, $R_5$, $R_6$, $R_7$ and $R_8$ have the meanings indicated for formula I, with the proviso that $R_1$ should be identical to $R_3$, $R_2$ should be identical to $R_4$ and $R_5$ should be identical to $R_6$.

a. The reaction of an acylisocyanide of the formula II with a hydrazone of the formula III according to process a) is suitably carried out at a temperature of $-20°$ to $150°C$, preferably at $0°$ to $80°C$. The reaction is suitably carried out in an inert solvent, preferably a hydrocarbon such as hexane, cyclohexane, benzene, toluene or xylene, in a halogenated hydrocarbon such as methylenechloride, chloroform, carbon tetrachloride or chlorobenzene, in an ether such as diethyl ether, diisopropyl ether, tetrahydrafurane or dioxane, in a carboxylic acid ester such as methyl acetate or ethyl acetate or in a nitrile such as acetonitrile. Furthermore the reaction is advantageously carried out in the presence of an acid acceptor, for example a tertiary amine, such as triethylamine or pyridine, or an inorganic base such as sodium hyroxide, sodium carbonate or sodium bicarbonate.

b. The reaction of an acylisocyanide of the formula II with a hydrazone of the formula IV according to process (b) is suitably carried out at a temperature of $-10°$ to $200°C$, preferably at $0°$ to $80°C$, in an inert solvent. The solvents already mentioned for process (a) are preferably used. Furthermore the reaction is advantageously carried out in the presence of an acid acceptor, preferably as indicated for use in process (a). The monohalogen compound thus obtained of the formula V can be isolated or preferably converted, without isolation, to the substituted diaminoguanidines of the formula I by the addition of a hydrazone of the formula VI, suitably under the conditions which have been described in the first stage of this process. So especially unsymmetrically substituted diaminoguanidines of the formula I are prepared.

The acylisocyanide-dichlorides of the formula II, used as the starting material for process (a) and process (b) can be obtained by chlorination of acylisothiocyanates, N-acyl-dithiocarbamic acid esters or N-acyl-dithiocarbonic acid ester-imides (compare Ber. 99, 239 (1966); DAS 1,178,422).

The hydrazones of the formulae III and VI are obtained by reacting an appropriate aldehyde or ketone with the appropriate hydrazine (compare Ber. 76, 1254 (1943)).

c. The reaction of a substituted diaminoguanidine of the formula VII with a halide or anhydride of the acid of the formula VIII and a carbonyl compound of the formula IX, according to process (c), is suitably carried out at a temperature of $-10°$ to $150°C$, preferably at $10°$ to $30°C$. The reaction is suitably carried out in a water-miscible solvent, preferably in an alcohol, such as methanol or ethanol, an acid amide such as dimethylformamide or a nitrile such as acetonitrile. Furthermore the reaction is advantageously carried out in the presence of an acid acceptor, preferably as indicated for use in process (a). After about 0.5 hours to 4 days, generally after 1 to 2 days, the reaction mixture is suitably acidified. It is advantageous to use an aqueous acid, for example an inorganic acid such as hydrochloric acid or sulphuric acid, or an organic acid such as acetic acid or trifluoroacetic acid for this acidification.

The new compounds are formed in good yields. They are crystalline and can advantageously be purified by recrystallisation from organic solvents, preferably methanol, ethanol, propanol, dimethylformamide, toluene or cyclohexane.

The compounds of the formula I are valuable medicaments. They have a marked effect against protozoa, especially against coccidiosis. They are, for example, considerably superior to the known Robencides (?) with regard to compatibility. The compounds of the formula I are therefore particularly suitable for the therapy and prophylaxis of coccidiosis in domestic animals such as pigs, calves, sheep and rabbits, and especially poultry such as hens and turkeys. The compounds of the formula I can, in principle, be administered as such to the animals to be protected from coccidiosis. However, the new active compounds are appropriately employed in a mixture with a suitable inert, pharmaceutically customary excipient. The customary mixtures of animal feedstuffs, for example those for poultry, can be used as the excipient for the treatment of animals. For this purpose an active compound of the formula I is suitably admixed, in a concentration of 5 to 750 ppm, preferably 15 to 100 ppm, with the feedstuff.

The invention therefore also relates to medicaments against diseases caused by protozoa, these medicaments being characterised in that they contain a compound of the formula I as the active compound, in addition to customary, medically acceptable additives. The invention further relates to the use of the compounds of the formula I for combating protozoa.

MANUFACTURING EXAMPLES, METHOD A

Example 1

Manufacture of 2-benzoyl-1,3-bis-(p-chlorobenzylideneamino)-guanidine 10.0 G of benzoylisocyanide-dichloride are added dropwise to a solution of 15.3 g of p-chlorobenzaldehyde hydrazone and 14 ml of triethylamine in 100 ml of methylenechloride at room temperature whilst stirring and the mixture is stirred for a further 2 hours at room temperature. The methylenechloride is evaporated in vacuo and the residue is recrystallised from alcohol.

The yield is 10.2 g of product with a melting point of 222°C.

The following compounds are manufactured analogously:

Example 2

2-(p-Chlorobenzoyl)-1,3-bis-(p-chlorobenzylideneamino)-guanidine, of melting point 218°, from p-chlorobenzaldehyde hydrazone and p-chlorobenzoylisocyanide-dichloride.

Example 3

2-(m-Chlorobenzoyl)-1,3-bis-(p-chlorobenzylideneamino)-guanidine of melting point 208°, from p-chlorobenzaldehyde hydrazone and m-chlorobenzoyliso-cyanide-dichloride

Example 4

2-(o-Chlorobenzoyl)-1,3-bis-(p-chlorobenzylideneamino)-guanidine from p-chlorobenzaldehyde hydrazone and o-chlorobenzoylisocyanide-dichloride

Example 5

2-(3,4-Dichlorobenzoyl)-1,3-bis-(p-chlorobenzylideneamino)-guanidine, of melting point 199°, from p-chlorobenzaldehyde hydrazone and 3,4-dichlorobenzoylisocyanide-dichloride

Example 6

2-(2,4-Dichlorobenzoyl)-1,3-bis-(p-chlorobenzylideneamino)-guanidine from p-chlorobenzaldehyde hydrazone and 2,4-dichlorobenzoylisocyanide-dichloride

Example 7

2-(2,5-Dichlorobenzoyl)-1,3-bis-(p-chlorobenzylideneamino)-guanidine from p-chlorobenzaldehyde hydrazone and 2,5-dichlorobenzoylisocyanide-dichloride

Example 8

2-(3,5-Dichlorobenzoyl)-1,3-bis-(p-chlorobenzylideneamino)-guanidine from p-chlorobenzaldehyde hydrazone and 3,5-dichlorobenzoylisocyanide-dichloride

Example 9

2-(2,6-Dichlorobenzoyl)-1,3-bis-(p-chlorobenzylideneamino)-guanidine from p-chlorobenzaldehyde hydrazone and 2,6-dichlorobenzoylisocyanide-dichloride

Example 10

2-(3-Bromo-4-chlorobenzoyl)-1,3-bis-(p-chlorobenzylideneamino)-guanidine from p-chlorobenzaldehyde hydrazone and 3-bromo-4-chlorobenzoylisocyanide-dichloride

Example 11

2-(p-Bromobenzoyl)-1,3-bis-(p-chlorobenzylideneamino)-guanidine from p-chlorobenzaldehyde hydrazone and p-bromobenzoylisocyanide-dichloride

Example 12

2-(p-Iodobenzoyl)-1,3-bis-(p-chlorobenzylideneamino)-guanidine from p-chlorobenzaldehyde hydrazone and p-iodobenzoylisocyanide-dichloride

Example 13

2-(p-Fluorobenzoyl)-1,3-bis-(p-chlorobenzylideneamino)-guanidine, of melting point 230°, from p-chlorobenzaldehyde hydrazone and p-fluorobenzoylisocyanide-dichloride

Example 14

2-(o-Fluorobenzoyl)-1,3-bis-(p-chlorobenzylideneamino)-guanidine from p-chlorobenzaldehyde hydrazone and p-fluorobenzoylisocyanide-dichloride

Example 15

2-(p-Trifluoromethylbenzoyl)-1,3-bis-(p-chlorobenzylideneamino)-guanidine from p-chlorobenzaldehyde hydrazone and p-trifluoromethylbenzoylisocyanide-dichcloride

Example 16

2-(m-Trifluoromethylbenzoyl)-1,3-bis-(p-chlorobenzylideneamino)-guanidine from p-chlorobenzaldehyde hydrazone and m-trifluoromethylbenzoylisocyanide-dichloride

Example 17

2-(p-Cyanobenzoyl)-1,3-bis-(p-chlorobenzylideneamino)-guanidine from p-chlorobenzaldehyde hydrazone and p-cyanobenzoylisocyanide-dichloride

Example 18

Manufacture of 2-(nitrobenzoyl)-1,3-bis-(p-chlorobenzylideneamino)-guanidine 14.05 G of p-chlorobenzaldehyde and 1.1 g of triethyl amine were dissolved in 100 ml of methylene chloride and 5.5 g of hydrazinehydrate were added dropwise in such a manner that the temperature did not exceed 40°C. After finishing the addition, the reaction mixture was stirred for 30 minutes, the organic phase was separated, washed with water and dried over sodium sulfate. A solution of p-chlorobenzaldehydehydrazone was so obtained.

To this solution 11 g of triethyl amine were added and a solution of 12.45 g of p-nitrobenzoylisocyanidedichloride in 20 ml of methylene chloride were added dropwise at 10°C while stirring. Then, the reaction mixture was stirred for an hour and then filtered. The residue was washed with 10 ml of methylene chloride, stirred with 200 ml of water, filtered off and dried. 15.7 g of product of melting point 223°C were obtained.

Example 19

2-(5-Chloro-2-nitrobenzoyl)-1,3-bis-(p-chlorobenzylideneamino)-guanidine from p-chlorobenzaldehyde hydrazone and 5-chloro-2-nitrobenzoylisocyanide-dichloride

Example 20

2-(4-Chloro-3-nitrobenzoyl)-1,3-bis-(p-chlorobenzylideneamino)-guanidine, of melting point 227°, from p-chlorobenzaldehyde hydrazone and 4-chloro-3-nitrobenzoylisocyanide-dichloride

Example 21

2-(p-Toluyl)-1,3-bis-(p-chlorobenzylideneamino)-guanidine, of melting point 224°, from p-chlorobenzaldehyde hydrazone and p-toluylisocyanide-dichloride

Example 22

2-(m-Toluyl)-1,3-bis-(p-chlorobenzylideneamino)-guanidine from p-chlorobenzaldehyde hydrazone and m-toluylisocyanide-dichloride

Example 23

2-(o-Toluyl)-1,3-bis-(p-chlorobenzylideneamino)-guanidine from p-chlorobenzaldehyde hydrazone and o-toluylisocyanide-dichloride

Example 24

2-(2,5-Dimethylbenzoyl)-1,3-bis-(p-chlorobenzylideneamino)-guanidine from p-chlorobenzaldehyde hydrazone and 2,5-dimethylbenzoylisocyanide-dichloride

Example 25

2-(2,4-Dimethylbenzyl)-1,3-bis-(p-chlorobenzylideneamino)-guanidine from p-chlorobenzaldehyde hydrazone and 2,4-dimethylbenzoylisocyanide-dichloride

Example 26

2-(3,4-Dimethylbenzoyl)-1,3-bis-(p-chlorobenzylideneamino)-guanidine from p-chlorobenzaldehyde hydrazone and 3,4-dimethylbenzoylisocyanide-dichloride

Example 27

2-(3,5-Dimethylbenzoyl)-1,3-bis-(p-chlorobenzylideneamino)-guanidine from p-chlorobenzaldehyde hydrazone and 3,5-dimethylbenzoylisocyanide-dichloride

Example 28

2-(2,3-Dimethylbenzoyl)-1,3-bis-(p-chlorobenzylideneamino)-guanidine from p-chlorobenzaldehyde hydrazone and 2,3-dimethylbenzoylisocyanide-dichloride

Example 29

2-(2,4,6-Trimethylbenzoyl)-1,3-bis-(p-chlorobenzylideneamino)-guanidine from p-chlorobenzaldehyde hydrazone and 2,4,6-trimethylbenzoylisocyanide-dichloride

Example 30

2-(2,4,5-Trimethylbenzoyl)-1,3-bis-(p-chlorobenzylideneamino)-guanidine from p-chlorobenzaldehyde hydrazone and 2,4,5-trimethylbenzoylisocyanide-dichloride

Example 31

2-(p-Ethylbenzoyl)-1,3-bis-(p-chlorobenzylideneamino)-guanidine from p-chlorobenzaldehyde hydrazone and p-ethylbenzoylisocyanide-dichloride

Example 32

2-(p-Hexylbenzoyl)-1,3-bis-(p-chlorobenzylideneamino)-guanidine from p-chlorobenzaldehyde hydrazone and p-hexylbenzoylisocyanide-dichloride

Example 33

2-(3-Chloro-4-methylbenzoyl)-1,3-bis-(p-chlorobenzylideneamino)-guanidine from p-chlorobenzaldehyde hydrazone and 3-chloro-4-methylbenzoylisocyanide-dichloride

Example 34

2-(p-Anisoyl)-1,3-bis-(p-chlorobenzylideneamino)-guanidine from p-chlorobenzaldehyde hydrazone and p-anisoylisocyanide-dichloride

Example 35

2-(m-Anisoyl)-1,3-bis-(p-chlorobenzylideneamino)-guanidine from p-chlorobenzaldehyde hydrazone and m-anisoylisocyanide-dichloride

Example 36

2-(o-Anisoyl)-1,3-bis-(p-chlorobenzylideneamino)-guanidine from p-chlorobenzaldehyde hydrazone and o-anisoylisocyanide-dichloride

Example 37

2-(p-Ethoxybenzoyl)-1,3-bis-(p-chlorobenzylideneamino)-guanidine from p-chlorobenzaldehyde hydrazone and p-ethoxybenzoylisocyanide-dichloride

Example 38

2-(p-Hexyloxybenzoyl)-1,3-bis-(p-chlorobenzylideneamino)-guanidine from p-chlorobenzaldehyde hydrazone and p-hexyloxybenzoylisocyanide-dichloride

Example 39

2-(2,4-Dimethoxybenzoyl)-1,3-bis-(p-chlorobenzylideneamino)-guanidine from p-chlorobenzaldehyde hydrazone and 2,4-dimethoxybenzoylisocyanide-dichloride

Example 40

2-(2,5-Dimethoxybenzoyl)-1,3-bis-(p-chlorobenzylideneamino)-guanidine from p-chlorobenzaldehyde hydrazone and 2,5-dimethoxybenzoylisocyanide-dichloride

Example 41

2-(3,5-Dimethoxybenzoyl)-1,3-bis-(p-chlorobenzylideneamino)-guanidine from p-chlorobenzaldehyde hydrazone and 3,5-dimethoxybenzoylisocyanide-dichloride

Example 42

2-(3,4-Dimethoxybenzoyl)-1,3-bis-(p-chlorobenzylideneamino)-guanidine from p-chlorobenzaldehyde hydrazone and 3,4-dimethoxybenzoylisocyanide-dichloride

Example 43

2-(Piperonyloyl)-1,3-bis-(p-chlorobenzylideneamino)-guanidine from p-chlorobenzaldehyde hydrazone and piperonyloylisocyanide-dichloride

Example 44

2-(3,4,5-Trimethoxybenzoyl)-1,3-bis-(p-chlorobenzylideneamino)-guanidine from p-chlorobenzaldehyde hydrazone and 3,4,5-trimethoxybenzoylisocyanide-dichloride

Example 45

1,3-Dimethyl-2-benzoyl-1,3-bis-(p-chlorobenzylideneamino)-guanidine from p-chlorobenzaldehyde methyl-hydrazone and benzoylisocyanide-dichloride

Example 46

1,3-Diethyl-2-benzoyl-1,3-bis-(p-chlorobenzylideneamino)-guanidine from p-chlorobenzaldehyde ethyl-hydrazone and benzoylisocyanide-dichloride

Example 47

1,3-Dibutyl-2-benzoyl-1,3-bis-(p-chlorbenzylideneamino)-guanidine from p-chlorobenzaldehyde butyl-hydrazone and benzoylisocyanide-dichloride

Example 48

2-Benzoyl-1,3-bis-(benzylideneamino)-guanidine, of melting point 145°, from benzaldehyde hydrazone and benzoylisocyanide-dichloride

Example 49

2-Benzoyl-1,3-bis-(p-bromobenzylideneamino)-guanidine, of melting point 239°, from p-bromobenzaldehyde hydrazone and benzoylisocyanide-dichloride

Example 50

2-Benzoyl-1,3-bis-(p-fluorobenzylideneamino)-guanidine, of melting point 153°C, from p-fluorobenzaldehyde hydrazone and benzoylisocyanide-dichloride

Example 51

2-Benzoyl-1,3-bis-(p-iodobenzylideneamino)-guanidine from p-iodobenzaldehyde hydrazone and benzoylisocyanide-dichloride

Example 52

2-Benzoyl-1,3-bis-(m-chlorobenzylideneamino)-guanidine, of melting point 161°C, from m-chlorobenzaldehyde hydrazone and benzoylisocyanide-dichloride

Example 53

2-Benzoyl-1,3-bis-(o-chlorobenzylideneamino)-guanidine from o-chlorobenzaldehyde hydrazone and benzoylisocyanide-dichloride

Example 54

2-Benzoyl-1,3-bis-(3,4-dichlorobenzylideneamine(sic))-guanidine, of melting point 213°, from 3,4-dichlorobenzaldehyde hydrazone and benzoylisocyanide-dichloride

Example 55

2-Benzoyl-1,3-bis-(2,4-dichlorobenzylideneamino)-guanidine, of melting point 232°, from 2,4-dichlorobenzaldehyde hydrazone and benzoylisocyanide-dichloride

Example 56

2-Benzoyl-1,3-bis-(p-cyanobenzylideneamino)-guanidine, of melting point 227°, from p-cyanobenzaldehyde hydrazone and benzoylisocyanide-dichloride

Example 57

2-Benzoyl-1,3-bis-(p-trifluoromethylbenzylideneamino)-guanidine from p-trifluoromethylbenzaldehyde hydrazone and benzoylisocyanide-dichloride

Example 58

2-Benzoyl-1,3-bis-(p-chloro-α-methylbenzylideneamino)-guanidine from p-chloroacetophenone hydrazone and benzoylisocyanide-dichloride

Example 59

2-(3-chloro-4-methoxy-benzoyl)-1,3-bis-(p-chlorobenzylideneamino)-guanidine of melting point 205° from p-chlorobenzaldehyde hydrazone and 3-chloro-4-methoxy-benzoyl-isocyanide-dichloride

Example 60

2-(m-nitrobenzoyl)-1,3-bis-(p-chlorobenzylideneamino)-guanidine of melting point 205° from p-chlorobenzaldehyde hydrazone and m-nitro-benzoyl-isocyanidedichloride

Example 61

2-(2-methyl-4-nitro-benzoyl)-1,3-bis-(p-chlorobenzylideneamino)-guanidine of melting point 208° from p-chlorobenzaldehyde hydrazone and 2-methyl-4-nitro-benzoylisocyanidedi-chloride

Example 62

2-(4-methyl-2-nitro-benzoyl)-1,3-bis-(p-chlorobenzylideneamino)-guanidine of melting point 184° from p-chlorobenzaldehyde hydrazone and 4-methyl-2-nitro-benzoyl-isocyanidedi-chloride

MANUFACTURING EXAMPLES, METHOD B

Example 63

Manufacture of 2-benzoyl-1-(p-chlorobenzylideneamino)-3-(p-bromobenzylideneamino)-guanidine A solution of 17.6 g of p-chlorobenzaldehyde hydrazone and 5.0 g of triethylamine in 50 ml of methylene chloride is added dropwise to a solution of 10.0 g of benzoylisocyanide-dichloride in 100 ml of methylene chloride at room temperature whilst stirring. The mixture is stirred for a further hour at room temperature. A solution of 10.0 g of p-bromobenzaldehyde hydrazone and 5.0 g of triethyleamine in 50 ml of methylene chloride is then added. The mixture is stirred for 2 hours at room temperature, the solvent is evaporated off and the residue is recrystallised from alcohol.

The following compounds are manufactured analogously:

Example 64

2-Benzoyl-1-(p-fluorobenzylideneamino)-3-(p-chlorobenzylideneamino)-guanidine from benzoylisocyanide-dichloride, p-chlorobenzaldehyde hydrazone and p-fluorobenzaldehyde hydrazone

Example 65

2-Benzoyl-1-(p-chlorobenzylideneamino)-3-(p-iodobenzylideneamino)-guanidine from benzoylisocyanide-dichloride, p-chlorobenzaldehyde hydrazone and p-iodobenzaldehyde hydrazone

Example 66

2-Benzoyl-1-(p-chlorobenzylideneamino)-3-(p-trifluoromethylbenzylideneamino)-guanidine from benzoylisocyanide-dichloride, p-chlorobenzaldehyde hydrazone and p-trifluoromethylbenzaldehyde hydrazone

Example 67

2-Benzoyl-1-(p-chlorbenzylideneamino)-3-(p-cyanobenzylideneamino)-guanidine from benzoylisocyanide-dichloride, p-chlorobenzaldehyde hydrazone and p-cyanobenzaldehyde hydrazone.

Example 68

1-Methyl-2-benzoyl-1,3-bis-(p-chlorobenzylideneamino)-guanidine from benzoylisocyanide-dichloride, p-chlorobenzaldehyde methyl-hydrazone and p-chlorobenzaldehyde hydrazone

Example 69

2-Benzoyl-1-(p-chlorobenzylideneamino)-3-(p-chloro-α-methylbenzylideneamino)-guanidine from benzoylisocyanide-dichloride, p-chloroacetophenone hydrazone and p-chlorobenzaldehyde hydrazone The compounds indicated in the Examples given for method a are manufactured analogously:

MANUFACTURING EXAMPLES, METHOD C

Example 70

Manufacture of 2-Benzoyl-1,3-bis-(p-chlorobenzylidenamino)-guanidine 1.4 G of benzoylchloride are added to a solution of 1.7 g of 1,3-bis-(isopropylideneamino)-guanidine, 3.1 g of p-chlorobenzaldehyde and 1.5 g of triethylamine in 30 ml of methylenechloride and the mixture is left to stand for 3 days at room temperature. The solvent is evaporated off and the residue dissolved in 10 ml of methanol and acidified with 2 N aqueous hydrochloric acid. After 3 hours at room temperature the crystals which have precipitated are filtered off and recrystallised from ethanol. 0.27 g of product of melting point 223°C is obtained.

The compounds indicated in the Examples given for method (a) are manufactured analogously.

We claim:

1. Substituted diaminoguanidines of the general formula I

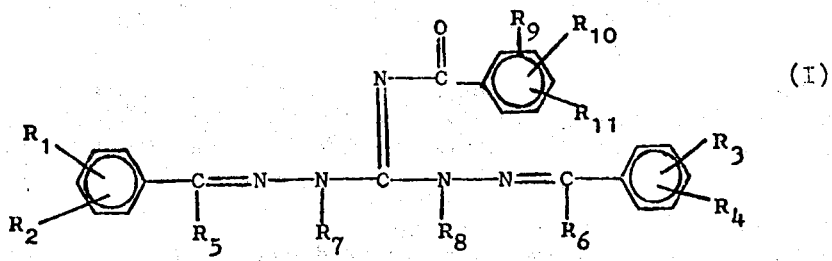

wherein $R_1$ and $R_3$ denote hydrogen, halogen, trifluoromethyl, $R_2$ and $R_4$ denote hydrogen or halogen, $R_5$, $R_6$, $R_7$ and $R_8$ denote hydrogen or alkyl with 1 to 6 C atoms, $R_9$ denotes hydrogen, halogen, alkyl or alkoxy with 1 to 6 C atoms in each case, trifluoromethyl or nitro, $R_{10}$ denotes hydrogen, halogen or alkyl or alkoxy with 1 to 6 C atoms in each case and $R_{11}$ denotes hydrogen, halogen or alkyl or alkoxy with 1 to 6 C atoms in each case and their pharmacologically acceptable salts.

2. Substituted diaminoguanidines of the formula I as claimed in claim 1, wherein $R_2$, $R_4$, $R_5$, $R_6$, $R_7$, $R_8$, $R_9$ and $R_{10}$ each is hydrogen, $R_1$ and $R_3$ each is para-chlorine and $R_{11}$ is hydrogen, para-chlorine, para-nitro or meta-nitro.

3. A compound as claimed in claim 1 which is 2-benzoyl-1,3-bis-(p-chlorobenzylidene-amino)-guanidine.

4. A compound as claimed in claim 1, which is 2-(p-chlorobenzoyl)-1,3-bis-(p-chlorobenzylideneamino)-guanidine.

5. A compound as claimed in claim 1, which is 2-(p-nitrobenzoyl)-1,3-bis-(p-chlorobenzylidene-amino)-guanidine.

6. A compound as claimed in claim 1, which is 2-(m-nitrobenzoyl)-1,3-bis-(p-chlorobenzylidene-amino)-guanidine.

7. A composition characterised in that it contains an effective amount for combatting diseases caused by protozoa of the compound of the formula I in claim 1 in a mixture with a pharmaceutically customary excipient or with a feedstuff mixture.

8. Method for combating diseases caused by protozoa comprising administering an effective amount of a compound of formula I in claim 1.

* * * * *